United States Patent
Belkhayat et al.

(10) Patent No.: US 11,759,204 B2
(45) Date of Patent: Sep. 19, 2023

(54) SYSTEMS, DEVICES, AND RELATED METHODS FOR FASTENING TISSUE

(71) Applicant: Boston Scientific Scimed, Inc., Maple Grove, MN (US)

(72) Inventors: Nora Belkhayat, Framingham, MA (US); Ryan V. Wales, Northborough, MA (US); Paul Smith, Smithfield, RI (US); Conor Reid, Cambridge, MA (US); Jeff Gray, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 393 days.

(21) Appl. No.: 16/921,644

(22) Filed: Jul. 6, 2020

(65) Prior Publication Data
US 2021/0007737 A1 Jan. 14, 2021

Related U.S. Application Data

(60) Provisional application No. 62/872,290, filed on Jul. 10, 2019.

(51) Int. Cl.
*A61B 17/072* (2006.01)
*A61B 17/068* (2006.01)
(Continued)

(52) U.S. Cl.
CPC ........ *A61B 17/072* (2013.01); *A61B 17/0686* (2013.01); *A61B 17/07207* (2013.01);
(Continued)

(58) Field of Classification Search
CPC ............... A61B 17/068; A61B 17/072; A61B 17/07207; A61B 17/115; A61B 17/00234;
(Continued)

(56) References Cited

U.S. PATENT DOCUMENTS 5,040,715 A * 8/1991 Green .............. A61B 17/07207
227/176.1
5,653,374 A * 8/1997 Young .............. A61B 17/07207
227/176.1
(Continued)

FOREIGN PATENT DOCUMENTS

EP 3195814 A1 7/2017
WO 2012019063 A2 2/2012

OTHER PUBLICATIONS

International Search Report and Written Opinion dated Oct. 26, 2020, in counterpart International Patent Application No. PCT/US2020/040907 (12 pages, in English).

*Primary Examiner* — Scott A Smith
(74) *Attorney, Agent, or Firm* — Bookoff McAndrews, PLLC (57) ABSTRACT

A medical device may include a shaft extending from a proximal end toward a distal end, the shaft including a lumen extending from the proximal end toward the distal end; a first stapling head at the distal end, the first stapling head configured to contain one or more staples, and the first stapling head having a block disposed within, and movable relative to, the first stapling head; a second stapling head at the distal end; and a pushing element extending through the lumen, the pushing element being movable from a first position to a second position, wherein transition of the pushing element from the first position to the second position urges the block to move toward second stapling head to deploy the one or more staples.

20 Claims, 8 Drawing Sheets

(51) Int. Cl.
  *A61B 17/115*  (2006.01)
  *A61B 17/29*   (2006.01)
  *A61B 34/30*   (2016.01)
  *A61B 90/30*   (2016.01)
  *A61B 90/00*   (2016.01)

(52) U.S. Cl.
  CPC .......... *A61B 17/068* (2013.01); *A61B 17/115* (2013.01); *A61B 34/30* (2016.02); *A61B 90/00* (2016.02); *A61B 90/30* (2016.02); *A61B 2017/07214* (2013.01); *A61B 2017/07228* (2013.01); *A61B 2017/07257* (2013.01); *A61B 2017/2933* (2013.01); *A61B 2217/005* (2013.01); *A61B 2217/007* (2013.01)

(58) Field of Classification Search
  CPC .......... A61B 2017/07214; A61B 2017/00271; A61B 2017/07228; A61B 34/30; A61B 34/31; A61B 17/29; A61B 2017/2927; A61B 2017/2933; A61B 2017/2944; A61B 90/00; A61B 90/30; A61B 90/361

USPC ..... 227/19, 176.1, 175.1, 180.1; 606/1, 139, 606/219
  See application file for complete search history.

(56) References Cited

U.S. PATENT DOCUMENTS

| | | | |
|---|---|---|---|
| 2005/0230453 A1* | 10/2005 | Viola ............... | A61B 17/07207 227/176.1 |
| 2010/0006620 A1* | 1/2010 | Sorrentino ....... | A61B 17/07207 227/176.1 |
| 2012/0138660 A1* | 6/2012 | Shelton, IV ........... | A61B 34/71 227/176.1 |
| 2013/0261661 A1* | 10/2013 | Piraka ................. | A61B 17/068 227/176.1 |
| 2015/0048141 A1 | 2/2015 | Felder et al. | |
| 2017/0189026 A1* | 7/2017 | Felder ................... | A61B 17/11 |
| 2018/0289371 A1 | 10/2018 | Wang et al. | |
| 2020/0246005 A1* | 8/2020 | Wang ............ | A61B 17/07207 |

* cited by examiner

SYSTEMS, DEVICES, AND RELATED METHODS FOR FASTENING TISSUE

CROSS-REFERENCE TO RELATED APPLICATIONS

This application claims the benefit of priority from U.S. Provisional Application No. 62/872,290, filed Jul. 10, 2019, which is incorporated by reference herein in its entirety.

TECHNICAL FIELD

Various aspects of the present disclosure relate generally to tissue fastening, including visualizing, retracting, and coupling tissue. More specifically, embodiments of the present disclosure relate to systems, devices, and related methods for stapling tissue, among other aspects.

BACKGROUND

Tissue fastening (e.g., stapling) is used in many laparoscopic procedures. These procedures often involve resecting portions or sections of tissue, followed by closing using staples. An example of a common procedure would be colorectal anastomosis. In hybrid surgeries where physicians use laparoscopic and endoscopic platforms to conduct a procedure, a rigid stapler is often used. Linear staplers include long rigid members which are incapable of being navigated through tortuous anatomy without causing trauma to the tissue. Physicians also are moving towards endoscopic, outpatient procedures, which would require endoscopic stapling.

It is with the above considerations in mind that the improvements of the present disclosure may be useful.

SUMMARY

Aspects of the present disclosure relate to, among other things, systems, devices, and methods for fastening tissue, e.g., a flexible endoscope platform with stapling capability. Each of the aspects disclosed herein may include one or more of the features described in connection with any of the other disclosed aspects.

In one aspect, the disclosure is directed to a medical device comprising a shaft extending from a proximal end toward a distal end, the shaft including a lumen extending from the proximal end toward the distal end; a first stapling head at the distal end, the first stapling head configured to contain one or more staples, and the first stapling head having a block disposed within, and movable relative to, the first stapling head; a second stapling head at the distal end; and a pushing element extending through the lumen, the pushing element being movable from a first position to a second position, wherein transition of the pushing element from the first position to the second position urges the block to move toward second stapling head to deploy the one or more staples.

The pushing element also includes a third position and a fourth position, before the pushing element is moved from the first position to the second position, movement of the pushing element from the third position to the fourth position causes the first stapling head to move toward the second stapling head. The shaft extends along a longitudinal axis, and the block and the first stapling head each are movable toward the second stapling head along a trajectory that is substantially perpendicular to the longitudinal axis. The second stapling head includes a planar face extending in a plane substantially perpendicular to the trajectory, wherein the planar face is an anvil configured to bend the one or more staples into tissue upon contact with the one or more staples. The medical device includes a first extension extending proximally from the first stapling head, the first extension having a first ramp at a proximal end; and a distal end of the pushing element includes a second ramp configured to slide against the first ramp when the pushing element is moved from the third position to the fourth position. The first ramp extends radially inwardly in a proximal direction; and the second ramp extends radially outwardly in a distal direction. An outer surface of the pushing element includes a protrusion, wherein the protrusion is configured to directly contact the block. The block includes a third ramp, and a distal end of the protrusion includes a fourth ramp configured to slide against the third ramp when the pushing element is moved from the first position to the second position. The third ramp extends radially inwardly in a proximal direction, and the fourth ramp extends radially outwardly in a distal direction. The medical device further includes a first extension extending proximally from the first stapling head, the first extension including a longitudinally extending first recess; and movement of the pushing element from the fourth position to the first position causes the protrusion to slide through the first recess. While the pushing element moves from the fourth position to the first position, the block remains stationary relative to the first stapling head. The first stapling head includes a second recess coaxial with the first recess; and movement of the pushing element from the first position to the second position causes a distal end of the protrusion to extend through the second recess and into contact with the block. The block is coupled to an inner surface of the first stapling head by one or more resilient members. The medical device further includes a second shaft movable from a first configuration to a second configuration, wherein: when the second shaft is in the first configuration, the first stapling head and the second stapling head are spaced apart from one another by a first distance; and in the second configuration, the second shaft is distal relative to the first configuration, and positions the first stapling head and the second stapling head at a second distance from one another; the second distance being less than the first distance. The medical device further includes a first extension extending proximally from the first stapling head, and a second extension extending proximally from the second stapling head, wherein the first extension and the second extension are coupled to one another at a joint, wherein the first and second extensions are movable between: a first configuration where the first stapling head and the second stapling head are spaced apart from one another by a first distance; and a second configuration where the first stapling head and the second stapling head are spaced apart from one another by a second distance, wherein the second distance is less than the first distance.

In another aspect, the disclosure is directed to a medical device comprising a shaft extending from a proximal end toward a distal end along a longitudinal axis, the shaft including: a first conduit extending from the proximal end toward the distal end; an expandable chamber coupled to the first conduit; and one or more staples coupled to the expandable chamber, wherein, delivery of fluid to the expandable chamber via the first conduit is configured to move the one or more staples toward a surface to deploy the one or more staples by contacting the one or more staples with the surface.

The shaft further includes a recess at least partially defined by the surface, and expansion of the expandable member moves the one or more staples into the recess. The medical device further includes a second conduit extending from the proximal end toward the distal end, wherein the distal end of the shaft is configured to articulate relative to the longitudinal axis when the second conduit is filled with a fluid. The medical device further includes an electroactive polymer extending along a portion of the shaft, wherein the distal end of the shaft is configured to articulate relative to the longitudinal axis when current is applied to the electroactive polymer.

In yet another aspect, the disclosure is directed to a medical device comprising a shaft extending from a proximal end toward a distal end along a longitudinal axis, the shaft including a lumen extending from the proximal end toward the distal end; a pushing element extending through the lumen, wherein distal movement of the pushing element along the longitudinal axis is configured to deploy one or more staples in a direction substantially perpendicular to the longitudinal axis of the shaft.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn to systems, devices, and methods for coupling, cutting, and resecting tissue, among other aspects. Reference will now be made in detail to aspects of the present disclosure, examples of which are illustrated in the accompanying drawings. Wherever possible, the same or similar reference numbers will be used throughout the drawings to refer to the same or like parts. The term "distal" refers to a portion farthest away from a user when introducing a device into a subject. By contrast, the term "proximal" refers to a portion closest to the user when placing the device into the subject. The term "tissue fastening" may refer, for example, to stapling, fixing, attaching, fastening, or otherwise joining two portions of tissue together. The term "fastener" may include staples, clips, elastic bands, suture, or any other fastener known in the art.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

FIGS. 1-6 illustrate an exemplary medical device 100 that may be used to staple tissue 20. In some embodiments, medical device 100 may be a surgical stapling apparatus configured to engage body tissue 20, apply one or a plurality of surgical fasteners thereto, and optionally form an incision in the fastened body tissue during minimally invasive surgical procedures, such as endoscopic procedures. Medical device 100 may be used to apply surgical clips or other fasteners, but will be primarily discussed in the context of applying staples.

Figure 1:
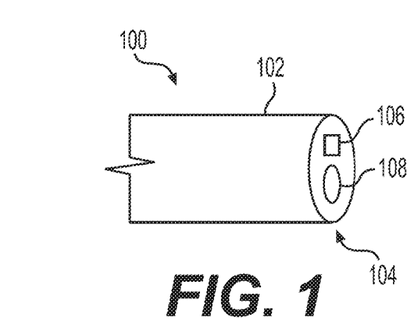
FIGS. 1-6 are illustrations of an exemplary stapling method, according to aspects of the present disclosure.
Figure 2:
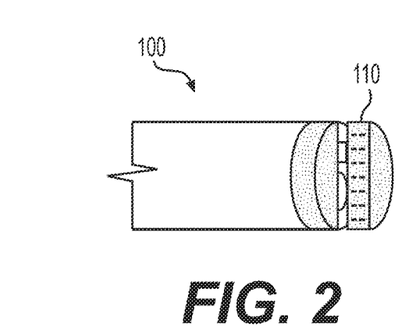
Figure 3:
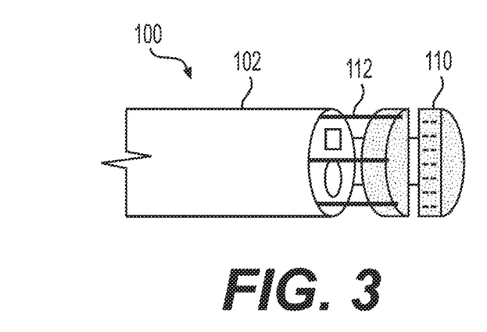

Medical device 100 may include an elongate member or shaft 102 that extends from a proximal end (not shown) toward a distal end 104. A stapling assembly 110 may be disposed at distal end 104. For clarity, medical device is shown in FIG. 1 without stapling assembly 110 attached. In some embodiments, stapling assembly 110 may be movable from a first position, such as a transporting position shown in FIG. 2, to a second position, such as an operating position shown in FIG. 3. In some examples, stapling assembly 110 may include one or more struts 112 coupled to distal end 104, or that are movable through lumens 108 of medical device 100. Stapling assembly 110 may not be operable in the transporting position shown in FIG. 2, and may be configured to deliver staples to tissue only when in the operating position shown in FIG. 3. Stated another way, medical device 100 may not be able to deploy staples or other tissue fastening elements when in a transporting position even in response to an action (e.g., pressing a button on an actuator) from an operator that would deploy the staples or tissue fastening elements when the medical device 100 is in the operating position.

Shaft 102 may be any suitable endoscopic member configured to bend and articulate so as to traverse tortuous anatomy in a body. Shaft 102 may be formed from one or more biocompatible materials, such as, e.g., HDPE, silicone, polyurethane, ETFE, SIBS, PIB-PUR, or any other suitable medical grade polymers, and may be flexible and configured to extend through tortuous anatomy. Shaft 102 may extend any length suitable for endoscopic or laparoscopic procedures, and may be configured to be positioned within a working channel of an endoscope. Or, shaft 102 may be positioned in the body without an endoscope. Shaft 102 may include illumination/optics assembly 106 and one or more lumens 108. Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

Assembly 106 may include an illumination device and an optics device. For example, the illumination device may include one or more of a fiber optic device (e.g., a light cable) or a light-emitting diode (LED) so as to provide illumination light to a location within a body of a subject distal of distal end 104. The optics device may include any appropriate device configured to provide a visual image of an internal location of the body of the subject. For example, the optics device may include one or more optical elements (e.g., lens, cameras, etc.).

The one or more lumens 108 may be arranged at any appropriate location about the distal end face of shaft 102. In some arrangements, the one or more lumens 108 may be arranged to provide irrigation and/or aspiration fluid. In such cases, the one or more lumens 108 may be fluidly coupled to one or more ports (not shown) of a handle (not shown). Such ports may be, in turn, fluidly coupled to one or more sources of irrigation and/or aspiration fluid for delivery via the one or more lumens 108. Further, the one or more lumens 108 may be arranged to receive one or more articulation wires (not shown) or the like for imparting selective articulation to at least distal end 104 of shaft 102. In one embodiment, a tool 114 may extend through lumen 108. Tool 114 may be configured to grasp tissue 20, and position tissue 20 within or adjacent to stapling assembly 110. For example, tool 114 may include a grasper, forceps, a snare, a clamp, a tissue loop, a helix coil, or a clip applier, or any other tool for performing a medical procedure.

Figure 4:
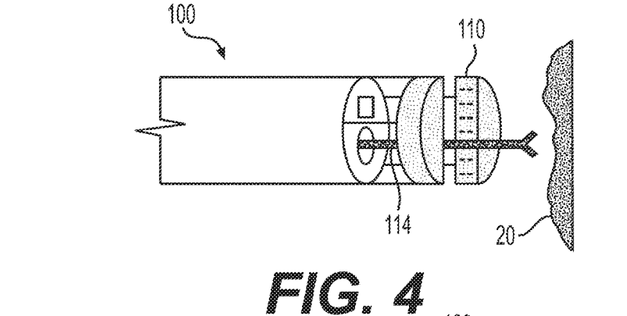
Figure 5:
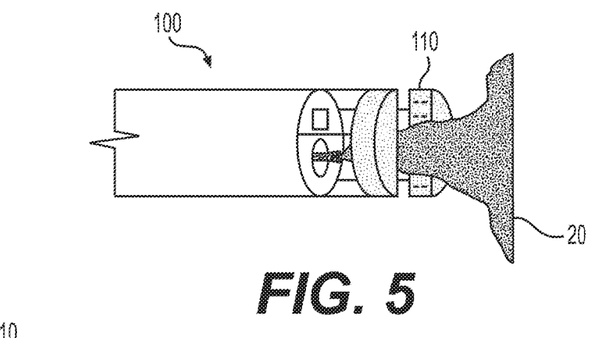
Figure 6:
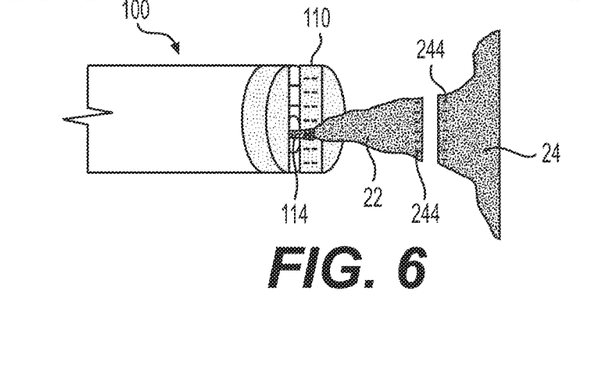
Figure 7:
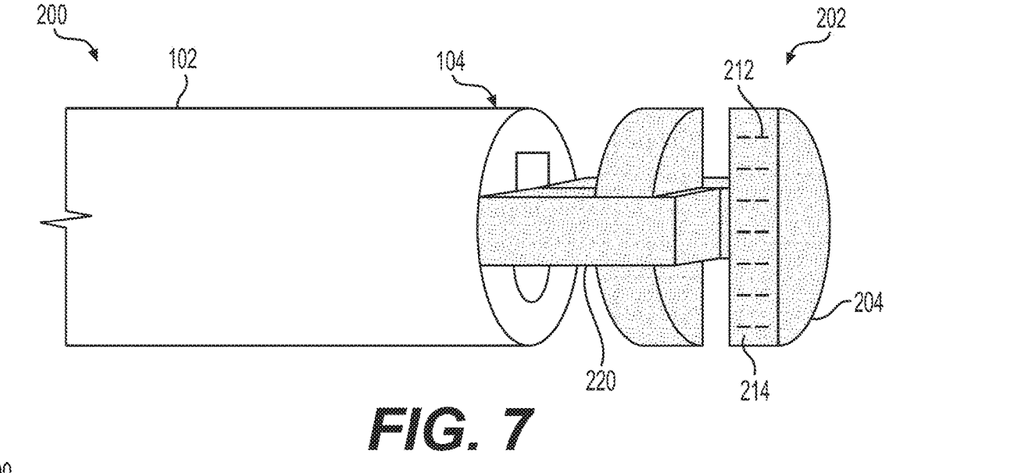
FIG. 7 is a perspective view a medical device according an embodiment of the present disclosure.

In FIG. 4, tool 114 is shown being extended toward tissue 20. In FIG. 5, tool 114 is shown positioning tissue 20 between adjacent stapling heads of stapling assembly 110. In FIG. 6, a first tissue portion 22 is shown with a first row of staples 244 deployed therein, while a second tissue portion 24 is shown with a second row of staples 244 deployed therethrough. The separate stapling heads of stapling assembly 110 may be moved together by actuation of a push button or other mechanism, which ejects a staple from one stapling head toward the other stapling head. Medical device 100 also may include one or more tools for separating stapled tissue portions, such as, e.g., a knife.

A medical device 200 is shown in FIGS. 7-12. Medical device 200 may include a shaft 102 as set forth in FIGS. 1-6. Medical device 200 may include one or more staples 244 (FIGS. 11 and 12) configured to be deployed along a trajectory that is substantially perpendicular to the longitudinal axis of shaft 102. Medical device 200 may include a navigation state (FIG. 2), where staples 244 may be positioned proximally to articulating portions of shaft 102. In the navigation state, the stapling heads of stapling assembly 110 are positioned close to the distal face of elongate member 102. The stapler is intended to be close to the face of elongate member 102, to make traversing through anatomy easier when not using the stapling function. The stapling heads of stapling assembly may rest in an open position (both in the navigation state and in the operating position) to maintain visualization. The stapling head may be pushed forward using a mechanical driving mechanism (e.g., driving wires, sheath, etc.) which may connected to the struts. The driving mechanism may extend through the scope to the proximal end to be actuated in the handle by a medical profession. Once medical device 200 is moved to a desired location, a tissue acquisition feature, e.g., tool 114 described with reference to FIGS. 1-6, located internal or external to shaft 102 can be used to acquire and position tissue for stapling.

In some embodiments, medical device 200 may include a stapling assembly 202 disposed at distal end 104. Stapling assembly 202 may include a first stapling head 204 that may be fixed to distal end 104, and a second stapling head 206 that may be movable relative to distal end 104. In other embodiments, first stapling head 204 and second stapling head 206 may be movable between a transporting configuration, and an operable configuration, in a similar manner as described above with reference to FIGS. 1-6. First stapling head 204 may include a flat face 214 that extends substantially perpendicular to a longitudinal axis of shaft 102. Flat face 214 may include one or more depressions 212, and may act as an anvil for the legs of staples 244. First stapling head 204 may be coupled to shaft 102 by a support 210. It is contemplated that support 210 may extend through one or more lumens of shaft 102 (i.e., a through-the-scope attachment), may be coupled to an exterior of shaft 102 (i.e., an over-the-scope attachment), or may include a combination of such attachments. First stapling head 204 also may include a curved radially outward facing surface opposite of flat face 214, and may generally have a half-moon shape, although other suitable shapes also are contemplated.

Figure 14:
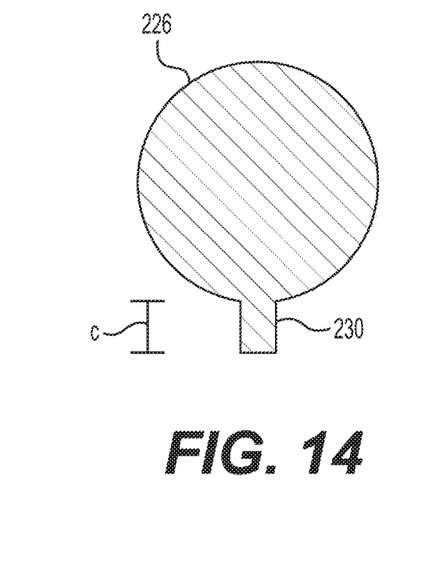
FIG. 14 is a cross-sectional view of a pushing element of the medical device of FIGS. 7-12.
Figure 15:
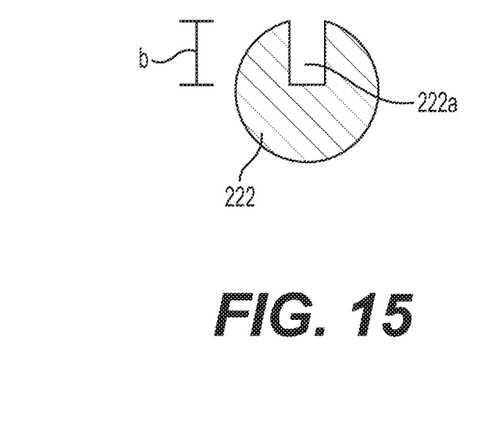
FIG. 15 is a cross-sectional view of an extension of the medical device of FIGS. 7-12.

Second stapling head 206 may be disposed within a housing 220 that is coupled to distal end 104. In some embodiments, housing 220 may be fixed to distal end 104 by a through-the-scope attachment, an over-the-scope attachment, or by a combination of attachment types. An extension 222 may extend proximally from second stapling head 206. The proximal end of extension 222 may include a ramped surface 224, which extends radially inward in the proximal direction. Extension 222 also may include a recess 222a formed in its outer surface (FIG. 15). A pushing element 226 may extend through lumen 108 of shaft 102. The distal end of pushing element 226 may include a ramped surface 228 that extends radially outward in the distal direction. Ramped surface 228 may be configured in any manner to engage with corresponding ramped surface 224 of the extension 222. Pushing element 226 also may include a protrusion 230 extending from its outer surface. The distal end of protrusion 230 may include a ramped surface 232 that extends radially outward in the distal direction (like ramped surface 228). Ramped surface 232 may be continuous with ramped surface 228 (i.e., may be coaxial or collinear), and may be proximal to an entirety of ramped surface 228). Recess 222a may be configured to receive protrusion 230, and may have a radial dimension b that is slightly longer or substantially equal to a dimension c that protrusion 230 extends from the outer surface of pushing element 226 (referring to FIGS. 14 and 15).

Figure 13:
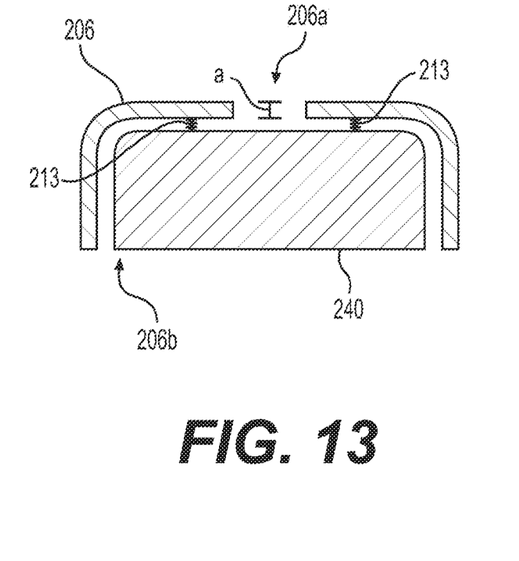
FIG. 13 is a cross-sectional view of a housing and a block of the medical device of FIGS. 7-12.

Referring to FIG. 13, second stapling head 206 may include a recess 206a that may be substantially coaxial with recess 222a. Second stapling head 206 also may include an opening 206b, which may be positioned adjacent to flat face 214 of first stapling head 204 during a stapling procedure. A block 240 may be disposed within second stapling head 206, and may be movable within second stapling head 206 and at least partially through opening 206b. Staples may be positioned beneath block 240 (e.g., in a cartridge), and when block 240 is pushed downward, the staples may be forced into anvils on the opposing staple head. Recess 206a may have a length/width dimension a that is less than dimension c of protrusion 230, so that protrusion 230 may extend through recess 206a to contact block 240. Block 240 may be biased toward a first configuration shown in FIG. 13, for example, by one or more resilient members or springs 213 attached to block 240 and to an inner surface of second stapling head 206. Two springs 213 are shown in FIG. 13 that are compressed in a resting state, although more or fewer springs also are contemplated. The springs 213 may be extended when protrusion 230 of pushing element 226 contacts and urges block 240 toward flat face 214 to deploy staples 244. Block 240 also may include a ramped surface 242 at its proximal end that extends radially inward in the proximal direction. Ramped surfaces 232 and 242 may cooperate with one another in a substantially similar manner to the manner in which ramped surfaces 224 and 228 cooperate with one another.

Figure 10:
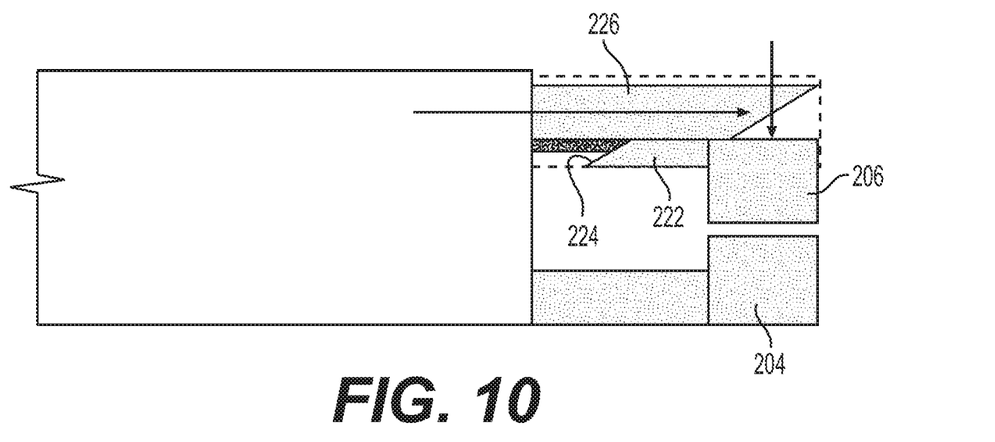
Figure 11:
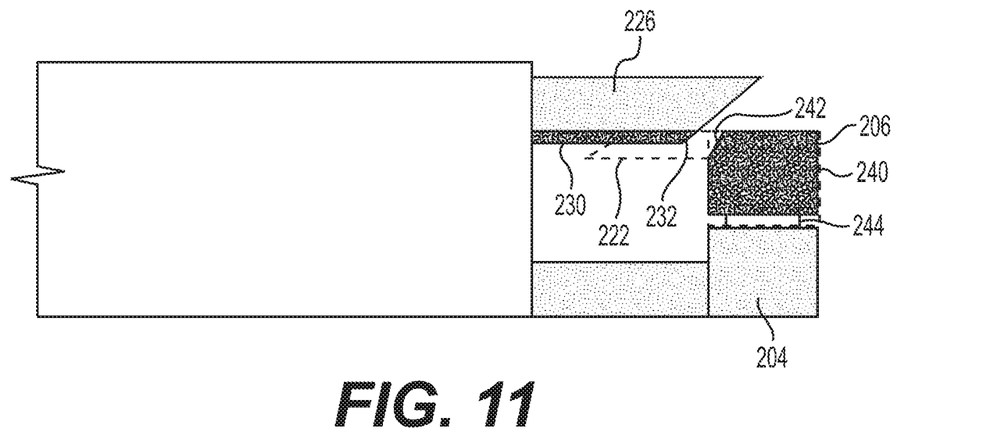
Figure 12:
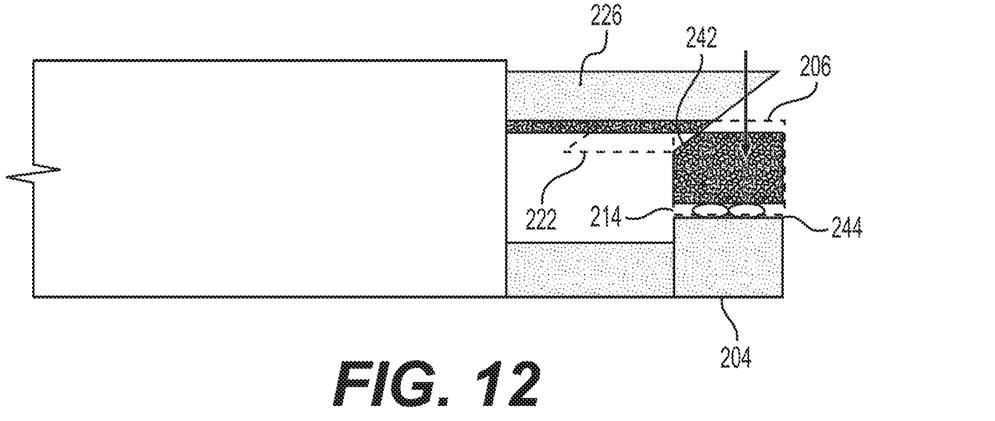

The various steps of operating medical device 200 will now be described. Ramped surfaces 224 and 228 may cooperate with one another such that when pushing element 226 is pushed distally along or parallel to a longitudinal axis of shaft 102, ramped surface 228 urges second stapling head 206 along a radially-inward directed path that is substantially perpendicular to the longitudinal axis of shaft 102 (see FIGS. 8 and 9). After second stapling head 206 reaches the end of its travel path and has travelled a predetermined first distance (toward first stapling head 204 in a direction perpendicular to the longitudinal axis of shaft 102), further distal movement of pushing element 226 may cause protrusion 230 to extend through recess 222a of extension 222 (e.g., FIG. 11). For at least a second predetermined distance, additional distal movement of pushing element 226 may cause protrusion 230 to slide, translate, or move relative to and/or through recess 222a without causing any movement of block 240 relative to second stapling head 206 (FIG. 11). In some embodiments, the second predetermined distance may correspond to or may be substantially equal to a length of recess 222a. However, after pushing element 226 has travelled the second predetermined distance, further distal movement of pushing element 226 may deploy block 240 containing one or more staples 244 (FIGS. 10 and 12). In particular, the further distal travel of pushing element 226 causes protrusion 230 to move through recess 206a and into contact with block 240. In particular, ramped surface 232 may slide against ramped surface 242 to urge block 240 toward first stapling head 204 (particularly toward flat face 214). Springs 213 may extend from the resting states during this movement of block 240. Block 240 may travel along a substantially similar trajectory that second stapling head 206 originally travelled (i.e., in a direction perpendicular to the longitudinal axis of shaft 102 and toward first stapling head 204).

Figure 16:
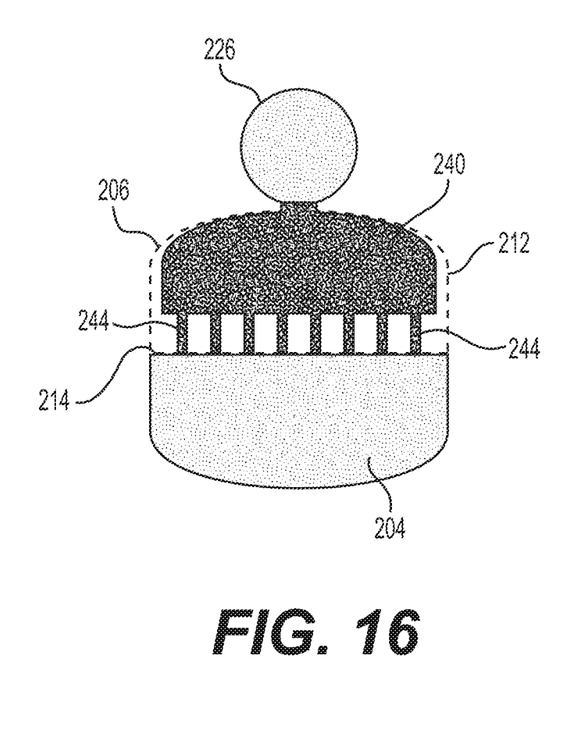
FIGS. 16 and 17 illustrate movement of the block of FIG. 13 to deploy one or more staples.
Figure 17:
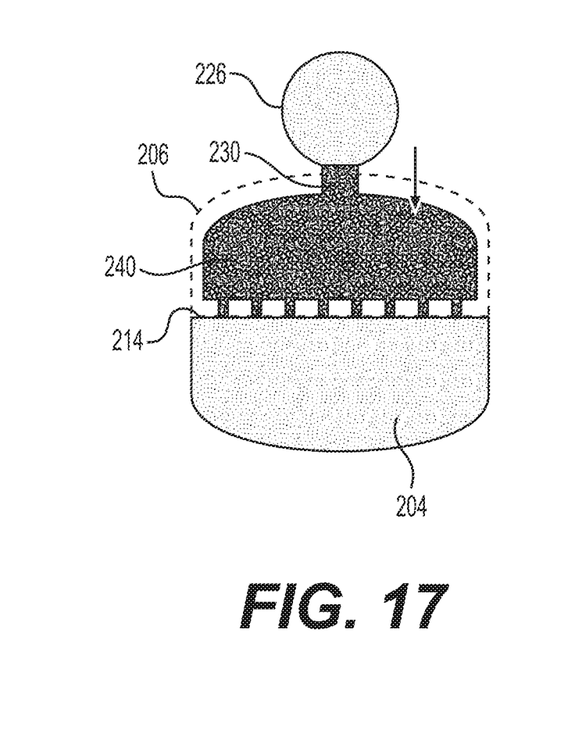

Urging block 240 toward flat face 214 may cause the legs of staples 244 to contact flat face 214 (see FIGS. 16 and 17), deploying staples 244 into tissue disposed between first stapling head 204 and second stapling head 206 (FIGS. 10 and 12). After the staple deployment is complete, a distally-directed force acting on pushing element 226 may be released (or reversed), causing springs 213 to move back to their resting, compressed configurations, and retracting block 240 into housing 206. Furthermore, the release (or reversal) of the distally directed force on pushing element 226 may cause the entirety of second stapling head 206 to move radially outward, along the path perpendicular to the longitudinal axis of shaft 102, to its original position.

Figure 8:
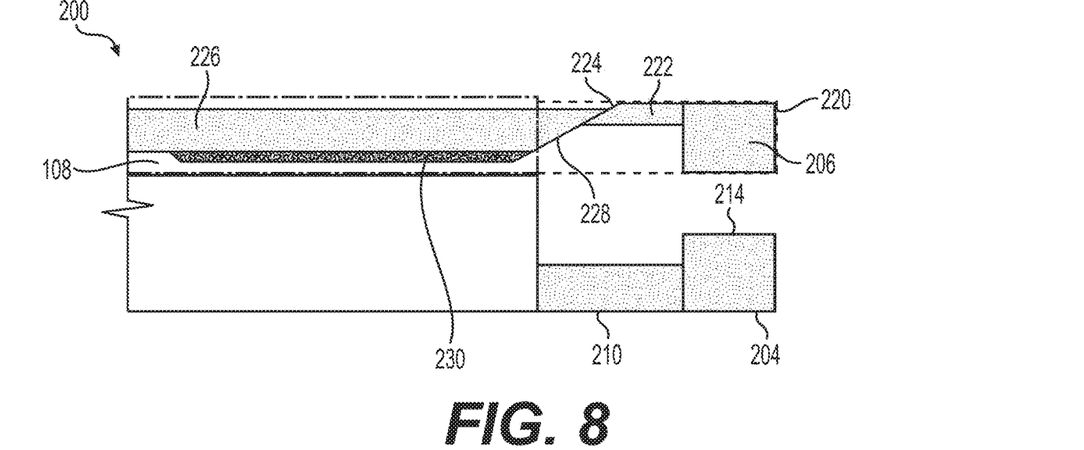
FIGS. 8-12 are side views illustrating a stapling procedure using the medical device of FIG. 7.
Figure 9:
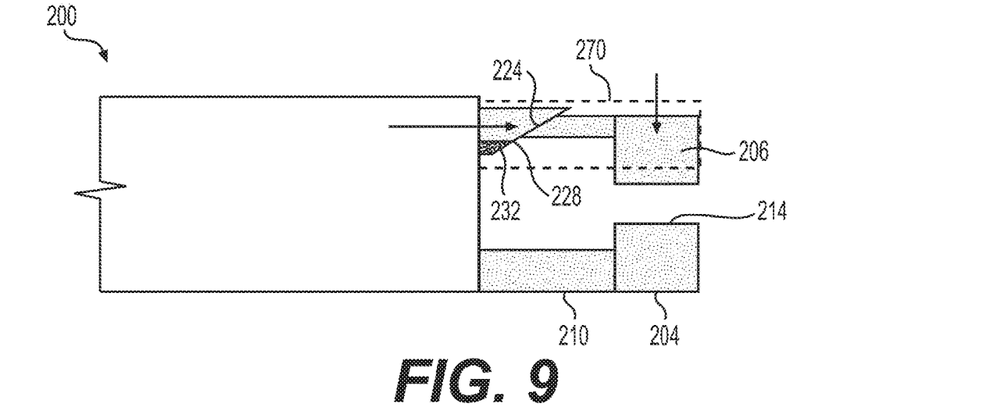

It is contemplated that movement of pushing element 226 from the position shown in FIG. 8, to the position shown in FIGS. 10 and 12 (after deployment of staple 244), may be performed with a single, smooth motion. However, in some embodiments, a stop may be included such that, at any time after second stapling head 206 has travelled the predetermined first distance (reached the end of its travel path toward first stapling head 204), a medical professional is required to perform some action to enable pushing element 226 to continue distally to drive block 240. The stop may, for example, be incorporated into recess 222a and may block movement of protrusion 230. In some embodiments, application of additional force to pushing element 226 may cause the stop to deform and move out of the path of pushing element 226. In other embodiments, movement of the stop may be controlled by an actuator, button, or the like, on a handle of the medical device. The inclusion of the stop may enable a medical professional to clamp tissue with only stapling heads 204 and 206, before needing to drive staples 244 through the tissue. This may help a medical professional readjust the clamped tissue sections when, for example, the wrong sections of tissue are grasped.

Figure 18:
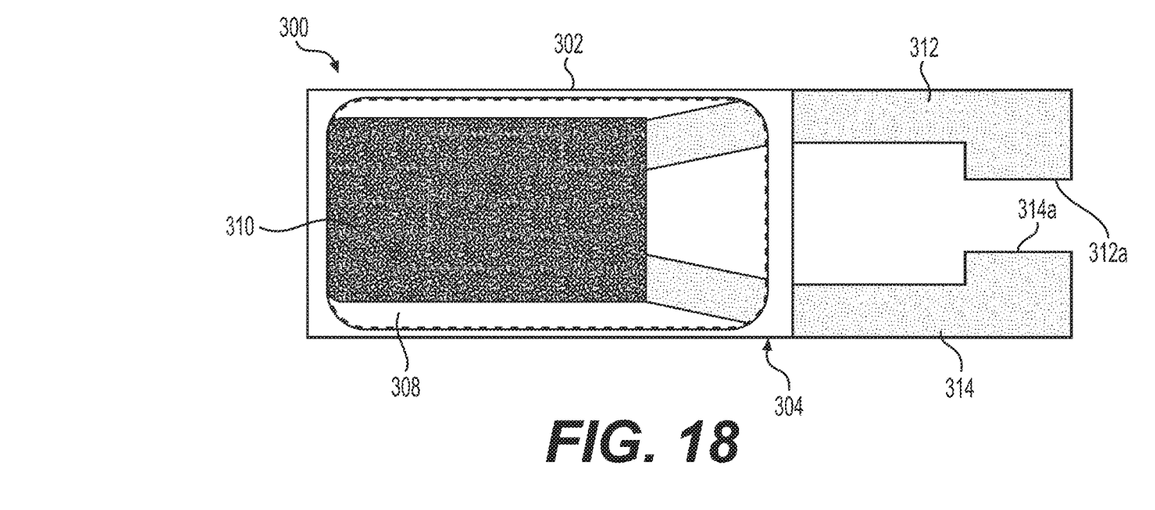
FIGS. 18 and 19 illustrate a medical device according to an alternative embodiment of the present disclosure.
Figure 19:
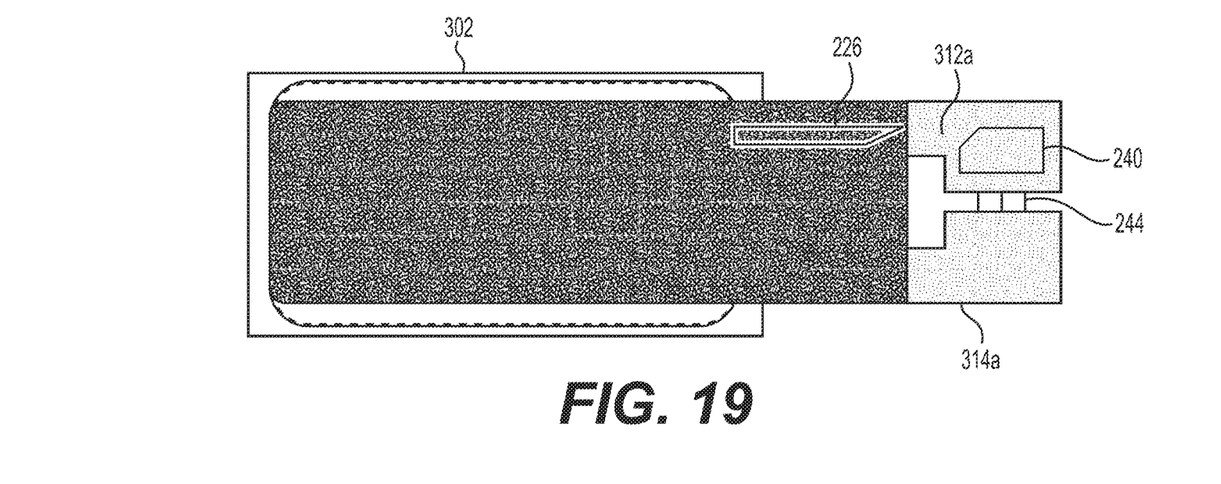

A medical device 300 is shown in FIGS. 18 and 19. Medical device 300 includes an alternative mechanism for moving two stapling heads closer to one another, where an outer shaft slides over the stapling heads to force them toward one another. For example, medical device 300 may include a shaft 302 extending from a proximal end (not shown) toward a distal end 304. A shaft 310 may extend within a lumen of shaft 302. Two stapling heads 312a and 314a may extend from the distal end of shaft 310 via supports 312 and 314, respectively. Supports 312 and 314 may extend both distally and radially outward (e.g., relative to a longitudinal axis of shaft 310) from the distal end of shaft 310. As shaft 302 is moved distally relative to shaft 310 (or shaft 310 and supports 312 and 314 are moved proximally relative to shaft 302), stapling heads 312a and 314a are moved toward one another along radially inwardly directed paths (FIG. 19). Once stapling heads 312a and 314a have reached the end of their travel paths such that they are substantially adjacent to one another, a second and separate staple deployment step may be carried out. It is contemplated that medical device 300 may include any other staple deployment mechanism disclosed herein. For example, a pusher element 226 may extend through support 312 and cause a block 240 (within, e.g., first stapling head 312a) to drive staples 244 into a surface of stapling head 314a. Alternatively, the fluid delivery mechanism described below with respect to FIGS. 22-24 may be utilized. In yet another embodiment, the closure of stapling heads 312a and 314a may itself deploy the staples 244.

Figure 20:
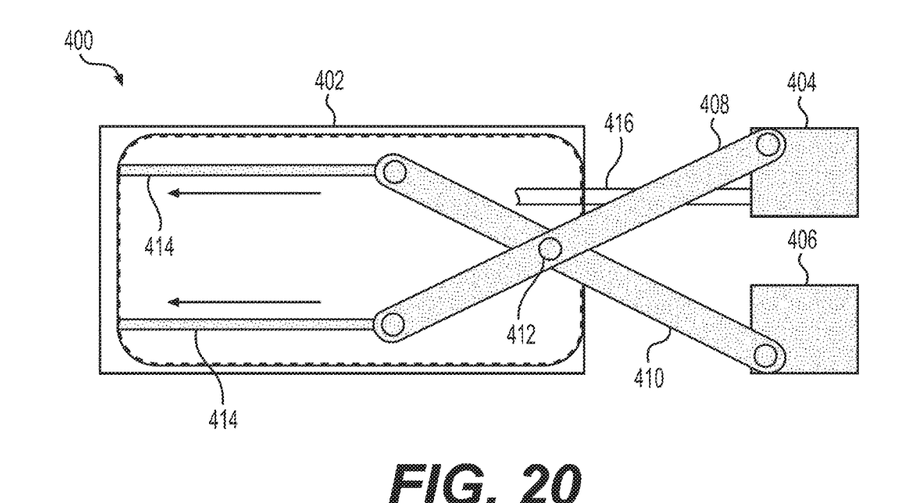
FIGS. 20 and 21 illustrate a medical device according to yet another alternative embodiment of the present disclosure.
Figure 21:
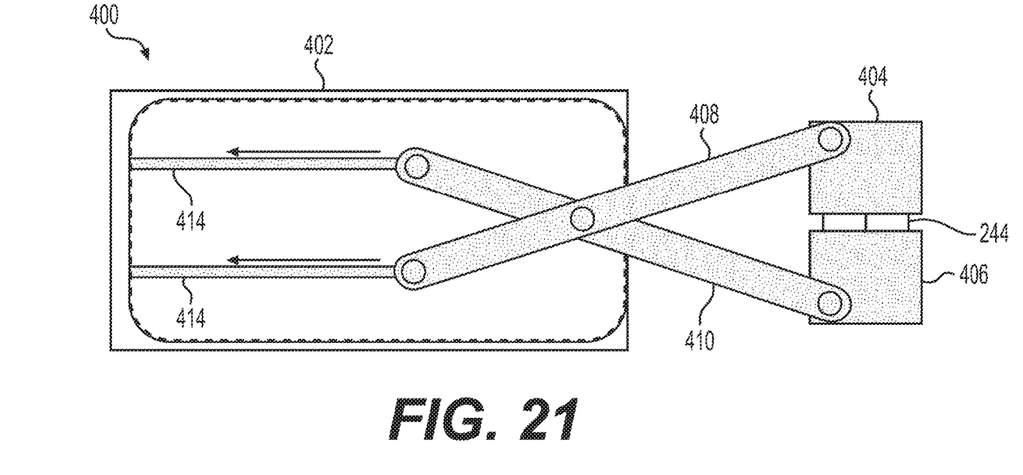

A medical device 400 is shown in FIGS. 20 and 21. Medical device 400 includes another alternative mechanism for closing two stapling heads, where wires are linked to a scissor joint attached to the stapling heads. For example, medical device 400 may include a shaft 402 extending from a proximal end (not shown) toward a distal end. Two stapling heads 404 and 406 may extend from the distal end of shaft 402 via supports 408 and 410, respectively. Supports 408 and 410 may extend proximally from their respective stapling heads, across one another and connected to one another at a joint 412 (e.g., a scissor joint, pivot, etc.). Wires or other actuating members 414 may extend proximally from each support 408 and 410. Actuation of the wires 414 may cause stapling heads 404 and 406 to move toward one another (FIG. 21). More specifically, proximal and radially inward directed forces may be applied to each wire 414. Because the working channel is small, pulling back on the wires may be sufficient to create the radially inward directed force necessary (so long as there is enough room for the wires to travel inward as they are pulled). The wires may be connected to a button or other actuation mechanism in the handle, so the user does not pull the wires directly. Once stapling heads 404 and 406 have reached the end of their travel paths and are adjacent to one another, a second and separate staple deployment step may be carried out. It is contemplated that medical device 400 may include any other staple deployment mechanism disclosed herein. For example, the fluid delivery mechanism described below with respect to FIGS. 22-24 may be utilized. For example, fluid may be delivered to, e.g., stapling head 404, via a conduit 416 to an expandable member (not shown) disposed within stapling head 404. In yet another embodiment, the closure of stapling heads 404 and 406 may itself deploy the staples 244.

Figure 22:
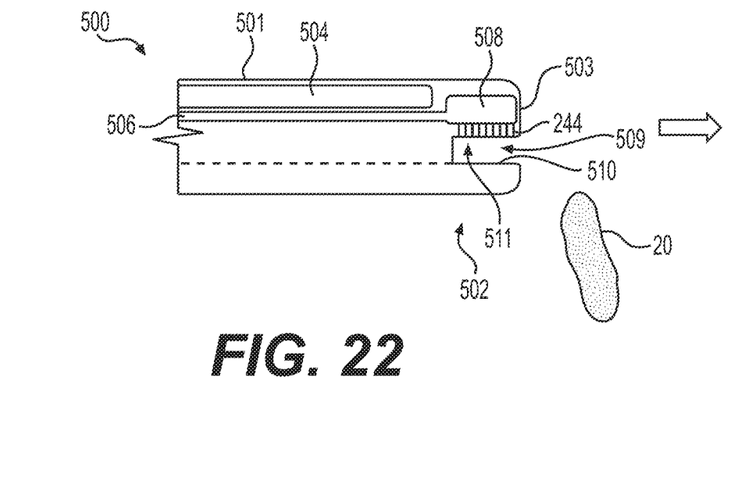
FIGS. 22-24 are illustrations of a medical device according to yet another alternative embodiment of the present disclosure.
Figure 23:
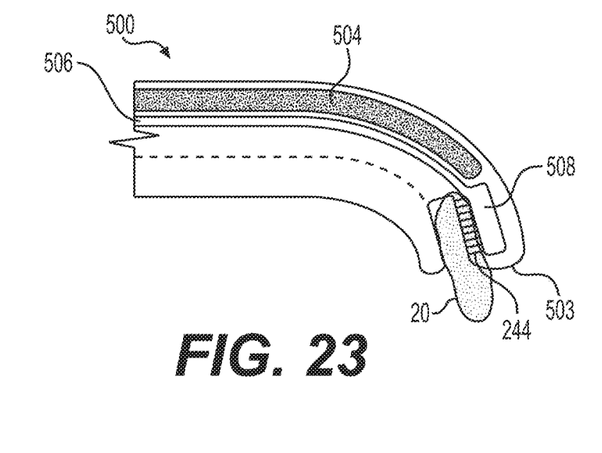
Figure 24:
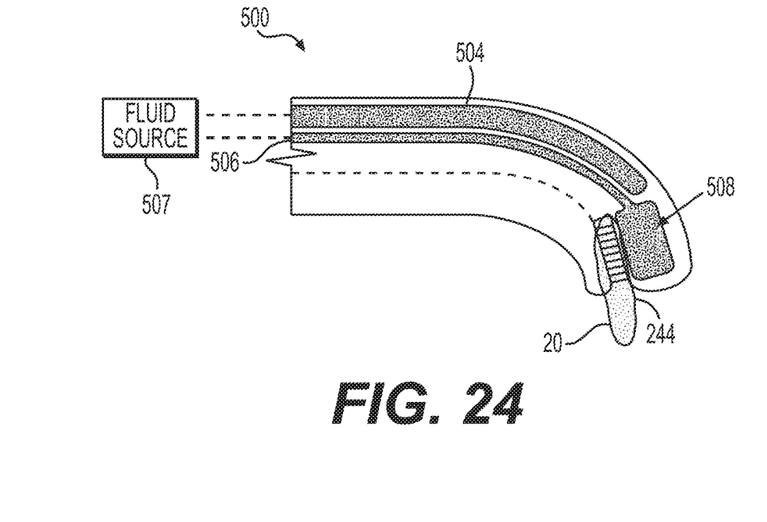

FIGS. 22-24 show an exemplary medical device 500 that may be used to staple tissue 20. Medical device 500 may include an elongate member or shaft 501 that extends from a proximal end (not shown) toward a distal end 502. Medical device 500 may include a distally-facing surface or end face 503 at distal end 502. Medical device 500 also may include a first fluid conduit 504 and a second fluid conduit 506. Second fluid conduit 506 may terminate at its distal end at an expandable chamber 508.

Expandable chamber 508 may be movable from a first configuration (shown in FIGS. 22 and 23) to a second configuration (shown in FIG. 24). Expandable chamber 508 may have a first volume in the first configuration, which is smaller than a second volume in a second configuration. The second volume may be 1.5, 2, 3, or more times larger than the first volume, although other suitable ratios also are contemplated. The exterior of expandable chamber may be formed by an expandable and resilient material, such as, e.g., rubber, polymers, or the like.

Medical device 500 also may include a recess 509 formed within distally-facing surface 503. However, it also is contemplated that recess 509 may be alternatively, or additionally, formed in a circumferential side surface of shaft 501. Recess 509 may be partially-defined by a flat surface 510 (which may act as an anvil during a stapling procedure). Expandable chamber 508 may be coupled to one or more staples 244, and may be arranged within distal end 502 such that the expansion of expandable chamber 508 is in the direction of recess 509. For example, solid and relatively stiff material may surround most portions of expandable chamber 508, while an opening 511 is disposed between expandable chamber 508 and recess 509. In this configuration, the expansion of expandable chamber 508 must be through opening 511 and into recess 509. Alternatively, expandable chamber 508 may not expand into recess 509 itself, but rather may drive staples 244 into and/or through recess 509 toward flat face 510. The driving of staples 244 into flat face 510 may occur along a trajectory that is substantially perpendicular to the plane of flat face 510.

First and second conduits 504, 506 may be coupled to a fluid source 507, configured to drive fluid through the conduits. Fluid source 507 may be a pump controlled by a controller. The pump may be any suitable pump, such as, e.g., a peristaltic pump, piston pump, motorized pump, microfluidic pump, infusion pump, or the like. The pump may be powered by electrical power, mechanical power, chemical power, or another suitable mechanism. Fluid source 507 may include a source (e.g., a reservoir) of fluid to be circulated through conduits 504, 506. In some examples, fluid source 507 may include a plurality of reservoirs, and may deliver fluid through each conduit 504, 506 from a dedicated reservoir. Alternatively, the same reservoir may supply both conduits 504, 506, and the flow may be controlled via one or more valves (not shown). The fluid circulated through conduits 504 and 506 may be any suitable biocompatible fluid, such as, e.g., sterile water or saline (in case of leaks). The controller may include a processor that is generally configured to accept information from the medical device and medical device components, and process the information according to various algorithms to produce control signals for controlling the fluid source 507. For example, the processor may accept information from the system and system components, process the information according to various algorithms, and produce information signals that may be directed to visual indicators, digital displays, audio tone generators, or other indicators of, e.g., a user interface, in order to inform a user of the system status, component status, procedure status or any other information that is being monitored by the system. The processor may be a digital IC processor, analog processor or any other suitable logic or control system that carries out the control algorithms. One or more pressure sensors may be coupled to each fluid conduit 504 and 506, and the controller may control the flow of fluid through conduits 504 and 506 by receiving and analyzing outputs from the one or more pressure sensors.

Articulation of medical device 500 may be achieved, at least in part, by filling first conduit 504 with fluid. Additionally, medical device 500 may be constructed to have a non-uniform stiffness. That is, medical device 500 may exhibit a tendency to bend in one or more directions, as opposed to one or more other directions. Stated another way, medical device 500 may be pre-disposed to articulate away from a longitudinal axis of shaft 501 along a particular trajectory. The tendency or pre-disposition to bend away from the longitudinal axis may be achieved by forming shaft 501 from at least two materials having different durometers or different hardness. In this embodiment, when first conduit 504 is filled with fluid, the portion of shaft 501 having a higher hardness would resist movement, and the portion of shaft 501 having a lower hardness would bend (e.g., as shown in FIGS. 23 and 24). In another embodiment, surface modifications such as, e.g., cuts, slits, recesses, or the like, may be made along only a portion of the outer circumference of shaft 501. Similarly, material may be removed from certain interior portions of shaft 501. When first conduit 504 fills with fluid in these embodiments, the portions of shaft 501 having surface modifications or otherwise having portions removed may bend, while portions of shaft 501 without such surface modifications or material removed may resist movement. Increasing the pressure within first conduit 504 may increase the articulation of shaft 501, while maintaining any particular pressure level may maintain the particular articulation angle.

Figure 25:
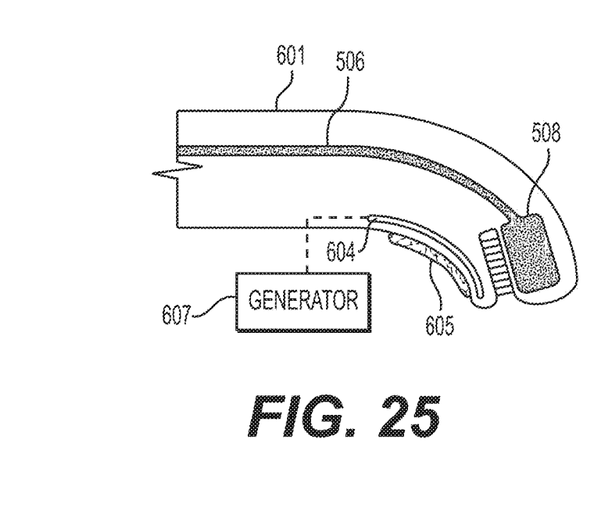
FIG. 25 is an illustration of a medical device according to yet another alternative embodiment of the present disclosure.

In yet another embodiment shown in FIG. 25, articulation of a shaft 601 may be achieved via the use of electroactive polymers 604, in place of the pressurized fluid. For example, such polymers 604 may contain cationic materials, which are randomly dispersed and without orientation. The surface on one side of shaft 601 adjacent to the polymer 604 may include anionic material 605. When an electrical current is activated in a generator 607 coupled to polymer 604, the cations in polymer 604 may orient and migrate towards the anionic material 605. This in turn may cause polymer 604 to bend. If the electrical current is flowing through polymer 604, shaft 601 maintains its bent configuration. In other words, the articulation of shaft 601 may be maintained during any cony cycle of an electrical generator coupled to the polymer. It also is contemplated that polymer 604 may include anionic materials, which are randomly dispersed and without orientation, and that material 605 includes cationic material. In still further examples, a magnetic attraction between polymer 604 and material 605 may be utilized to achieve the articulation.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a shaft extending from a proximal end toward a distal end, the shaft including a lumen extending from the proximal end toward the distal end;
a first stapling head at the distal end, the first stapling head configured to contain one or more staples, and the first stapling head having a block disposed within, and movable relative to, the first stapling head;
a second stapling head at the distal end; and
a pushing element extending through the lumen, the pushing element being movable from a first position to a second position, wherein transition of the pushing element from the first position to the second position urges the block to move toward the second stapling head to deploy the one or more staples, and wherein movement of the pushing element causes the first stapling head to translate toward the second stapling head along a trajectory that is substantially perpendicular to a longitudinal axis of the shaft.

2. The medical device of claim 1, wherein the pushing element also includes a third position and a fourth position, before the pushing element is moved from the first position to the second position, movement of the pushing element from the third position to the fourth position causes the first stapling head to move toward the second stapling head.

3. The medical device of claim 2, wherein the trajectory is a first trajectory, and wherein the block translates toward the second stapling head along a second trajectory that is substantially perpendicular to the longitudinal axis.

4. The medical device of claim 3, wherein the second stapling head includes a planar face extending in a plane substantially perpendicular to the trajectory, wherein the planar face is an anvil configured to bend the one or more staples into tissue upon contact with the one or more staples.

5. The medical device of claim 2, wherein:
the medical device includes a first extension extending proximally from the first stapling head, the first extension having a first ramp at a proximal end; and
a distal end of the pushing element includes a second ramp configured to slide against the first ramp when the pushing element is moved from the third position to the fourth position.

6. The medical device of claim 5, wherein:
the first ramp extends radially inwardly in a proximal direction; and
the second ramp extends radially outwardly in a distal direction.

7. The medical device of claim 2, wherein an outer surface of the pushing element includes a protrusion, wherein the protrusion is configured to directly contact the block.

8. The medical device of claim 7, wherein the block includes a third ramp, and a distal end of the protrusion includes a fourth ramp configured to slide against the third ramp when the pushing element is moved from the first position to the second position.

9. The medical device of claim 8, wherein the third ramp extends radially inwardly in a proximal direction, and the fourth ramp extends radially outwardly in a distal direction.

10. The medical device of claim 7, wherein:
the medical device further includes a first extension extending proximally from the first stapling head, the first extension including a longitudinally extending first recess; and
movement of the pushing element from the fourth position to the first position causes the protrusion to slide through the first recess.

11. The medical device of claim 10, wherein, while the pushing element moves from the fourth position to the first position, the block remains stationary relative to the first stapling head.

12. The medical device of claim 11, wherein:
the first stapling head includes a second recess coaxial with the first recess; and
movement of the pushing element from the first position to the second position causes a distal end of the protrusion to extend through the second recess and into contact with the block.

13. The medical device of claim 1, wherein the block is coupled to an inner surface of the first stapling head by one or more resilient members.

14. The medical device of claim 1, further including a second shaft movable from a first configuration to a second configuration, wherein:
when the second shaft is in the first configuration, the first stapling head and the second stapling head are spaced apart from one another by a first distance; and
in the second configuration, the second shaft is distal relative to the first configuration, and positions the first stapling head and the second stapling head at a second distance from one another, the second distance being less than the first distance.

15. A medical device, comprising:
a shaft extending from a proximal end toward a distal end along a longitudinal axis, the shaft including a lumen extending from the proximal end toward the distal end;
a first stapling head at the distal end, the first stapling head configured to contain one or more staples;
a second stapling head at the distal end; and
a pushing element extending through the lumen, wherein the pushing element includes a first ramped surface and a protrusion having a second ramped surface, wherein distal movement of the pushing element along the longitudinal axis is configured to cause the first ramped surface to contact a surface of the first stapling head, thereby causing the first stapling head to move toward the second stapling head, wherein distal movement of the pushing element along the longitudinal axis is further configured to cause the second ramped surface to contact a surface of a block within the first stapling head, thereby deploying one or more staples in a direction substantially perpendicular to the longitudinal axis of the shaft, and wherein the protrusion and the pushing element move jointly in all configurations of the medical device.

16. The medical device of claim 15, wherein the first ramped surface engages with an extension extending proximally from the first stapling head to cause the first stapling head to move toward the second stapling head, and wherein the protrusion extends through a recess of the extension to contact the surface of the block.

17. A medical device, comprising:
- a shaft extending from a proximal end toward a distal end, the shaft including a lumen extending from the proximal end toward the distal end;
- a first stapling head at the distal end, the first stapling head configured to contain one or more staples, and the first stapling head having a block disposed within, and movable relative to, the first stapling head;
- a second stapling head at the distal end; and
- a pushing element extending through the lumen, wherein:
  - the pushing element is movable from a first position to a second position, wherein transitioning the pushing element from the first position to the second position causes the pushing element to engage an extension extending proximally from the first stapling head, thereby causing the first stapling head to move toward the second stapling head; and
  - the pushing element is movable from a third position to a fourth position, after moving from the first position to the second position, wherein transitioning the pushing element from the third position to the fourth position causes a protrusion of the pushing element to extend through a recess of the extension to engage the block, thereby urging the block to move toward the second stapling head to deploy the one or more staples.

18. The medical device of claim 17, wherein the pushing element includes a first ramped surface configured to engage a second ramped surface of the extension, and wherein the protrusion includes a third ramped surface configured to engage a fourth ramped surface of the block.

19. The medical device of claim 17, wherein the protrusion and the pushing element move jointly in all configurations of the medical device.

20. The medical device of claim 17, wherein the first stapling head translates toward the second stapling head in a direction that is substantially perpendicular to a longitudinal axis of the shaft.

* * * * *